US008608691B2

(12) United States Patent
Pierpont (10) Patent No.: US 8,608,691 B2
(45) Date of Patent: Dec. 17, 2013

(54) ANGIOPLASTY METHOD AND MEANS FOR PERFORMING ANGIOPLASTY (75) Inventor: Brien E. Pierpont, St. Petersburg, FL (US)

(73) Assignee: Pierpont Family Limited Partnership, St. Petersburg, FL (US)

(*) Notice: Subject to any disclaimer, the term of this patent is extended or adjusted under 35 U.S.C. 154(b) by 1218 days.

(21) Appl. No.: 11/867,168

(22) Filed: Oct. 4, 2007

(65) Prior Publication Data
US 2008/0021383 A1 Jan. 24, 2008

Related U.S. Application Data (63) Continuation-in-part of application No. 10/773,925, filed on Feb. 6, 2004, now abandoned.

(60) Provisional application No. 60/446,001, filed on Feb. 7, 2003.

(51) Int. Cl.
A61M 29/00 (2006.01)
A61M 5/178 (2006.01)

(52) U.S. Cl.
USPC .............. 604/104; 604/164.03; 604/164.13; 604/167.03

(58) Field of Classification Search
USPC ............ 604/101.01, 101.03–101.05, 103.05, 604/164.09–164.11, 164.13, 604/167.01–167.06, 104, 164.03; 606/191, 606/194
See application file for complete search history.

(56) References Cited

U.S. PATENT DOCUMENTS

| 3,395,710 A | 8/1968 | Stratton et al. |
| 4,581,017 A | 4/1986 | Sahota |
| 4,744,366 A | 5/1988 | Jang |
| 4,771,777 A | 9/1988 | Horzewski et al. |
| 4,832,028 A | 5/1989 | Patel |
| 4,932,959 A | 6/1990 | Horzewski et al. |
| 4,944,745 A | 7/1990 | Sogard et al. |
| 4,988,356 A | 1/1991 | Crittenden et al. |
| 5,019,042 A | 5/1991 | Sahota |
| 5,035,705 A | 7/1991 | Burns |
| 5,059,178 A | 10/1991 | Ya |
| 5,085,636 A | 2/1992 | Burns |
| 5,102,390 A | 4/1992 | Crittenden et al. |
| 5,158,540 A | 10/1992 | Wijay et al. |
| 5,178,608 A | 1/1993 | Winters |
| 5,180,367 A | 1/1993 | Kontos et al. |

(Continued)

FOREIGN PATENT DOCUMENTS

| EP | 0415332 A1 | 3/1991 |
| EP | 0565996 A1 | 10/1993 |

Primary Examiner — Nicholas Lucchesi
Assistant Examiner — Nathan R Price
(74) Attorney, Agent, or Firm — Zarley Law Firm, P.L.C.

(57) ABSTRACT

An angioplasty procedure wherein a balloon dilatation catheter is movably positioned within an anchoring catheter and which in turn is located within a guiding catheter or wherein a balloon dilatation catheter is movably positioned within a guiding catheter and the anchoring catheter in turn is positioned on the external surface of the guiding catheter, or wherein a balloon dilatation catheter is movably positioned within a catheter which serves both as a guiding catheter and anchoring catheter. Additionally, valve elements are attached to the guiding and anchoring catheters to provide points of securement between the catheters and the balloon dilatation catheter and to prevent the backflow of blood through the catheter assembly. Actuation of the valve elements allows a doctor to control the movement of the catheters.

13 Claims, 8 Drawing Sheets

(56) References Cited

U.S. PATENT DOCUMENTS

| | | |
|---|---|---|
| 5,299,575 A | 4/1994 | Sandridge |
| 5,484,412 A | 1/1996 | Pierpont |
| 5,489,271 A | 2/1996 | Andersen |
| 5,554,118 A | 9/1996 | Jang |
| 6,398,799 B2 | 6/2002 | Kramer |
| 6,695,858 B1 | 2/2004 | Dubrul et al. |
| 2001/0016725 A1* | 8/2001 | Valley et al. .................. 604/509 |
| 2002/0165574 A1 | 11/2002 | Ressemann et al. |
| 2002/0165598 A1 | 11/2002 | Wahr et al. |

* cited by examiner

Fig. 1

Prior Art

ANGIOPLASTY METHOD AND MEANS FOR PERFORMING ANGIOPLASTY

BACKGROUND OF THE INVENTION

Cardiac catheterization and angioplasty are common medical procedures. The coronary arteries are vessels which supply the heart muscle with blood and are located on the outside surface of the heart. In order to visually examine the coronary arteries, a contrast agent has to be injected into the vessels before x-ray pictures can be taken of them. This is accomplished through a procedure called cardiac catheterization. This contrast agent is delivered through a catheter, which is a small hollow tube. This catheter is advanced to the heart under x-ray guidance, usually being inserted at the level of the groin into the femoral artery. This is accomplished through a needle which is first advanced into the femoral artery and subsequently the catheter is passed through the needle into the blood vessel or femoral artery. The femoral artery in turn is a tributary of the great vessel originating in the heart and therefore the catheter can be passed in a retrograde fashion under x-ray guidance very easily back to the origin of the coronary arteries.

Once the catheter is positioned at the origin of the coronary arteries, a dye syringe is placed on the end of the catheter remaining outside the patient and injections are performed with simultaneous x-ray pictures being taken.

An angioplasty procedure is similar in technique but more invasive, by the fact that a smaller catheter with a deflated balloon on its tip is advanced through the catheter which is positioned at the origin of the coronary artery and advanced down into the coronary artery to the site of where the vessel is narrowed. The balloon dilatation catheter is not advanced down the coronary artery by itself; however, first, a very small guide wire is advanced down the coronary artery, across the narrowed segment and then advanced further down into the coronary artery, beyond the narrowed segment. The balloon dilatation catheter is then advanced over the guide wire to the site of the narrowing. The guide wire allows the balloon dilatation catheter to track over it, thereby facilitating advancement of the balloon dilatation catheter down the vessel and thus preventing damage to the vessel wall. Once the balloon is positioned at the site of the narrowing in the vessel, the balloon is inflated by means of a hand held balloon inflation device. The balloon is inflated for generally 30 to 90 seconds and then deflated and withdrawn. This compresses the fatty-like material which is responsible for narrowing the coronary artery and opens the vessel, allowing for proper blood flow to the heart muscle.

At times it is difficult to advance the balloon dilatation catheter to the site of the narrowing, as these vessels are not always straight and often times bends in the vessel have to be negotiated before reaching the point of narrowing. Frequently, the balloon dilatation catheter cannot be easily advanced and the guiding catheter which is housing the balloon dilatation catheter and the guide wire comes loose from its position at the origin of the coronary artery and does not provide enough structural support or backup to allow advancement of the balloon dilatation catheter to the narrowed site.

Improvements in this field have been made such as for example, the angioplasty method and means for performing angioplasty seen in U.S. Pat. No. 5,484,412. Specifically, in this patent a method and means is provided using a plurality of different catheters that are all interconnected using a plurality of balloons to provide more accurate handling and control to improve angioplasty procedures. Despite this improved means and method additional improvements are desired. Specifically, a need exists for the use of non inflatable equipment that accomplishes similar results.

Thus, the principal object of the present invention is to provide an improved method and means for performing an angioplasty that provides structural support to the guiding catheter.

Another object of the invention is to provide catheter designs having the capability of proximal embolic protection.

These and other objects, features, or advantages of the present will become apparent from the specification and claims.

BRIEF SUMMARY OF THE INVENTION

This invention comprises an angioplasty procedure wherein the balloon dilatation catheter is movably positioned within an anchoring catheter which in turn is located within a guiding catheter. Optional internal balloons in the anchoring catheter can be inflated to secure the balloon dilatation catheter to the inside of the anchoring catheter. External balloons on the anchoring catheter can be inflated to anchor it to the inside of the guiding catheter and to the inside of the coronary artery. The external fixation balloons can be selectively inflated and deflated from the internal fixation balloons.

Additionally attached to the guiding catheter is a valve element that comprises a valve stem with threads and a valve opening therein such that the balloon dilation catheter can be passed through the valve opening such that when the valve is turned the balloon dilatation catheter is secured within the opening to secure the balloon dilatation catheter to the guide catheter. Alternatively, an anchoring catheter may be used with a similar valve element such that the balloon dilatation catheter can be secured to the anchoring catheter in a similar manner. Additionally the anchoring catheter or the guide catheter can be made of an inner and outer sheath that is attached distally to expandable material such that as the outer sheath and inner sheath slide over each other the material radially retracts or expands accordingly.

The method of this invention inserts a conventional guiding catheter into the origin of the coronary artery, (coronary ostium). A conventional guide wire and balloon dilatation catheter are then inserted through the anchoring catheter which in turn is inserted through the guiding catheter. Once the anchoring catheter is properly positioned in the proximal portion of the coronary artery and fixed in position with the use of external fixation balloon(s), the anchoring catheter is then secured to the guiding catheter using a valve element such that the dilatation catheter can be slid though the anchoring catheter and guide catheter along the guide wire until the dilatation balloon attached to the dilatation catheter is adjacent a plaque area of the blood vessel. At this time the dilatation balloon may be inflated.

DETAILED DESCRIPTION OF THE PREFERRED EMBODIMENT

Figure 1:
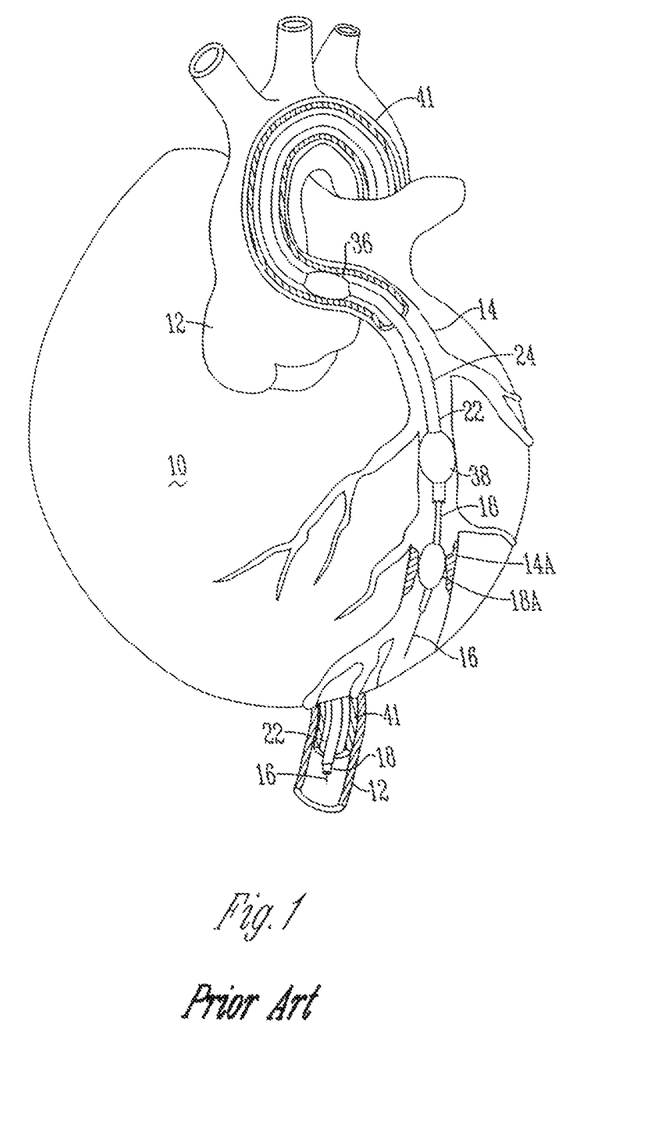
FIG. 1 is a schematic view of a human heart with the apparatus of this invention inserted into a coronary artery.

FIG. 1 shows a schematic view of a heart muscle 10 connected to the primary blood supply vessel 12 (aorta). A coronary artery 14 is also depicted in FIG. 1. The numeral 14A in FIG. 1 shows the plaque or obstruction in the coronary artery 14.

FIG. 1 also shows a first embodiment of a catheter system similar to that shown in U.S. Pat. No. 5,484,412 to Pierpont. The '412 reference is incorporated herein. In general the catheter system includes a conventional guide wire 16 over which a balloon dilatation catheter 18 is slidably mounted. Catheter 18 has an inflatable balloon 18A on the distal end thereof. Catheter 18 has its internal diameter divided by a membrane to create a balloon inflation passageway and a guide wire passageway 20 as is taught in the '412 reference.

The catheter system also includes an anchoring catheter 22 having a side wall 24 with an internal balloon 30 to secure the anchoring catheter to the balloon dilatation catheter 18. The side wall 24 also has a side port 31 for connection to a manifold that allows pressure monitoring, injection of saline to allow flushing and aspiration and injection of contrast to visualize the vessel. Extending from the outer wall 24 are first and second concentric external balloons 36 and 38 to provide a means to secure the anchoring catheter to a guide catheter 41 and blood vessel wall.

FIGS. 2-7 show several catheter systems that represent improvements over the catheter system shown in FIG. 1. Specifically FIGS. 2-7 show several different embodiments of how the guide catheter 41 and anchor catheter 22 may be secured and connected using inner and outer sheaths 24A and 24B, a valve element 44 (FIGS. 8 and 9) or a combination of both.

Figure 8:
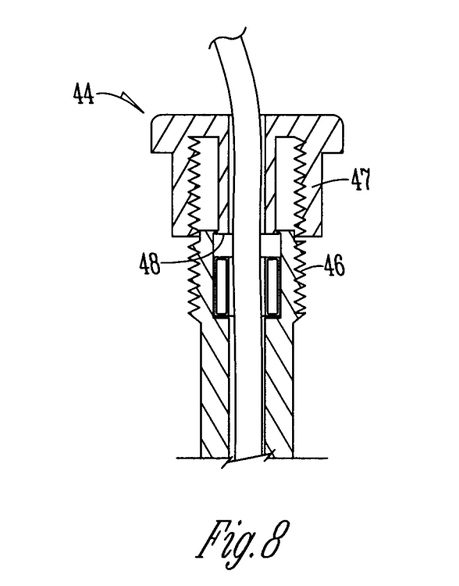
FIG. 8 is a sectional view of a valve element.
Figure 9:
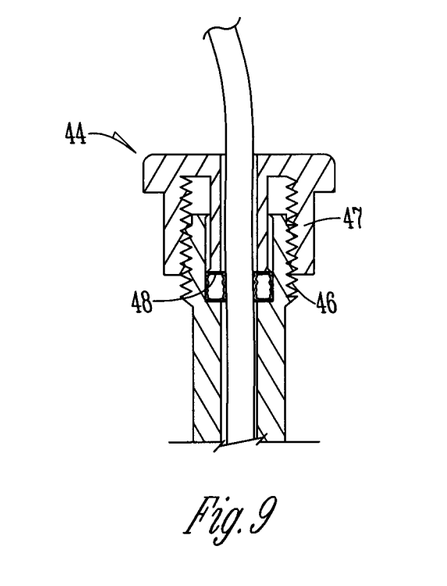
FIG. 9 is a sectional view of a valve element.

As best shown in FIGS. 8 and 9 the valve element 44 has a threaded stem 46 that threadably engages a threaded receptacle 47 that surrounds and is on the proximal end of the guide catheter 41 or anchor catheter 22. The stem 46 has a valve opening 48 therein such that as the stem 46 is turned in a clockwise position on the threaded receptacle 47 the opening prevents fluid flow through the body wherein if turned in a counter clockwise position the valve opening 48 opens to allow fluid communication through the valve element 44. In one embodiment this valve element 44 is a thouey-borst® valve that is known in the angioplasty art. Typically, the valve element 44 is used to prevent the back flow of blood through the fluid passageway in which the valve element 44 is inserted.

In the embodiments of FIGS. 2-7 the valve element is additionally used to function as a securing device. Specifically, when the valve element 44 is attached to the anchor catheter 22 the balloon dilatation catheter 18 is able to be disposed through the valve opening 48 such that when the stem 46 is turned in a clockwise position the valve element 44 closes on the balloon dilatation catheter 18 and thus secures the balloon dilatation catheter 18 to the anchoring catheter 22. In such an arrangement not only does the valve element 44 prevent back flow of blood it additionally acts as a securing device to help with the control of catheters used during an angioplasty.

Figure 2:
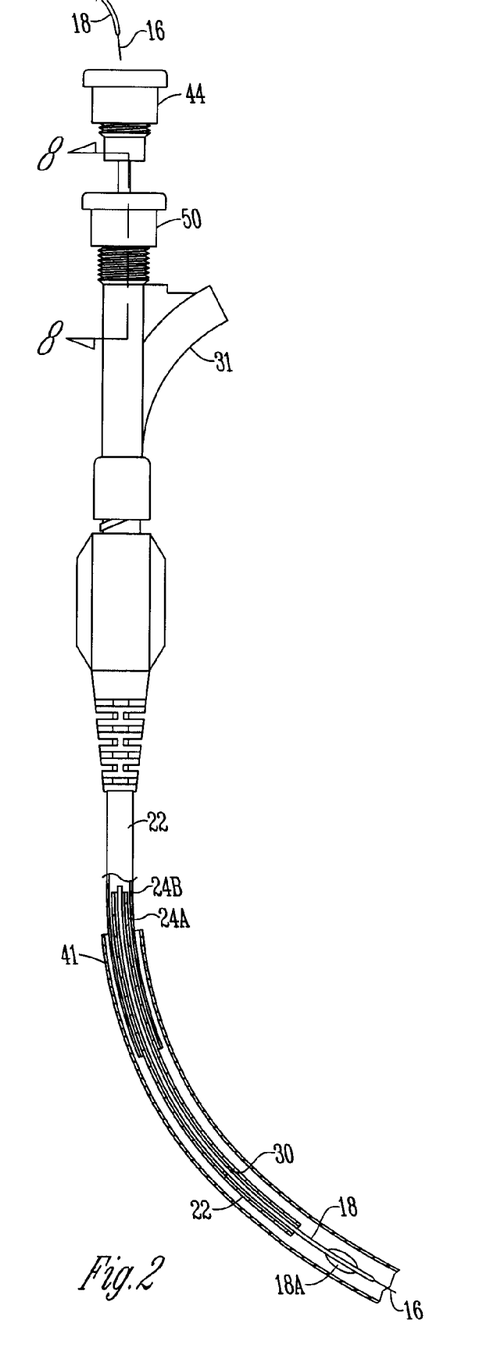
FIG. 2 is an enlarged scale sectional view of a catheter assembly.

FIG. 2 shows an embodiment wherein the anchoring balloons 36 and 38 are eliminated. Specifically, the side outer wall 24 of anchoring catheter 22 has inner and outer sheaths 24A and 24B that slide over each other. Expandable material is disposed between the inner and outer sheaths 24A and 24B and radially retracts and expands as the outer and inner sheaths slide back and forth over each other. By radially expanding the expandable material the material can engage the guide catheter 41 or blood vessel to secure the anchoring catheter 22 to each. In this manner the external balloons 36 and 38 may be eliminated. Though in another embodiment the balloons 36 and 38 could remain to provide an additional securing means.

Figure 3:
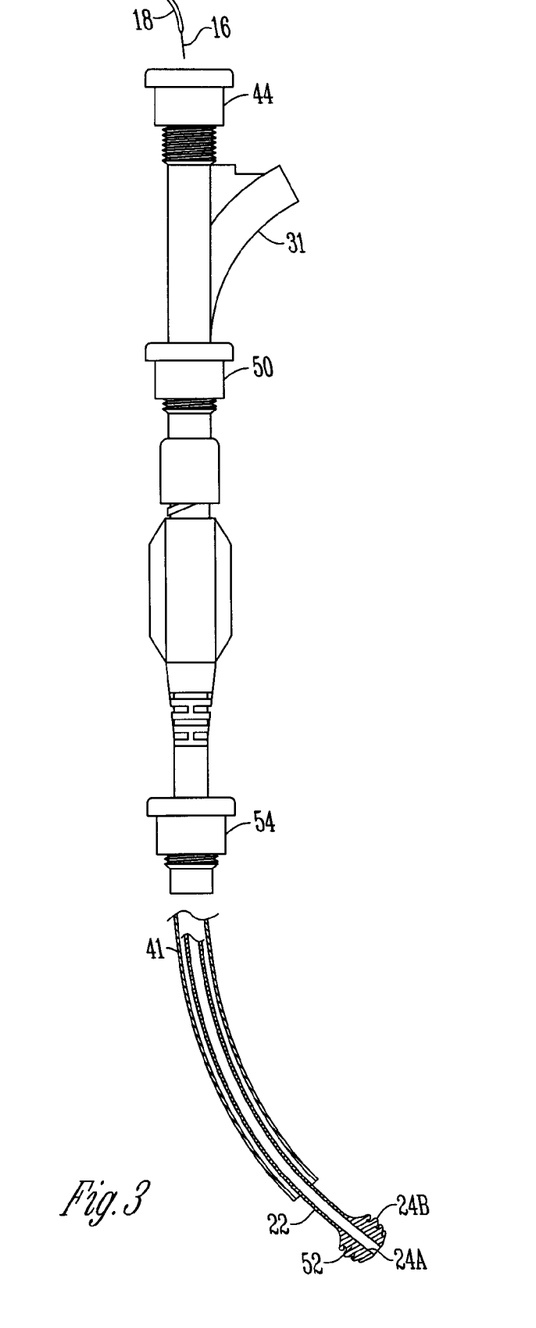
FIG. 3 is an enlarged scale sectional view of a catheter assembly.

FIG. 3 is a variation of FIG. 2 in that the anchoring catheter 22 comprises inner sheath 24A and outer sheath 24B wherein the inner sheath extends past the outer sheath at the proximal end and has a section of expandable material 52 at the distal end. The section of expandable material 52 acts similarly to inflatable balloon 38 wherein inflated the external balloon 38 temporarily occludes or blocks blood flow through the coronary artery 14. Unless the selected embodiment of anchoring catheter 22 includes optional perfusion ports either located proximal or proximal and distal to the external balloon 38. Similarly, the section of expandable material 52 occludes or blocks blood flow through the coronary artery 14 unless the selected embodiment of anchoring catheter 22 includes optional perfusion ports located proximal or proximal and distal to the section of expandable material 52 or is established through the section of expandable material 52 being made porous.

Temporary occlusion at a vessel location proximal to targeted obstruction 14A is useful to prevent distal embolization by plaque debris that may be dislodged during an angioplasty and subsequently entrained in the blood flow. Proximal occlusion to prevent distal embolization typically includes the aspiration of potentially contaminated blood following dilation, but prior to either deflating balloon 38 or contracting the section of expandable material 52 which allows blood flow to resume. Aspiration can be performed through an interior lumen of anchoring catheter 22 by drawing a partial vacuum at the proximal end thereof, using for example, a syringe. If aspiration is difficult, a flush solution can be injected through the interior lumen of the anchoring catheter 22 before aspirating.

Further, in the embodiment of FIG. 3 a valve element 44 is placed on the proximal end of the inner sheath 24A, a second valve element 50 is placed on the proximal end of the outer sheath 24B and a third valve element 54 is placed on the proximal end of the guiding catheter. Thus, when the first valve element 44 is turned in a clockwise position and the balloon dilation catheter 18 is disposed therethrough, the balloon dilation catheter 18 is secured to the inner sheath 24A. Similarly, when the second valve element 50 is rotated clockwise the outer sheath 24B is secured to the inner sheath 24A just as when the third valve element 54 is rotated in a clockwise position the outer sheath 24B is secured to the guide catheter 41.

Figure 4:
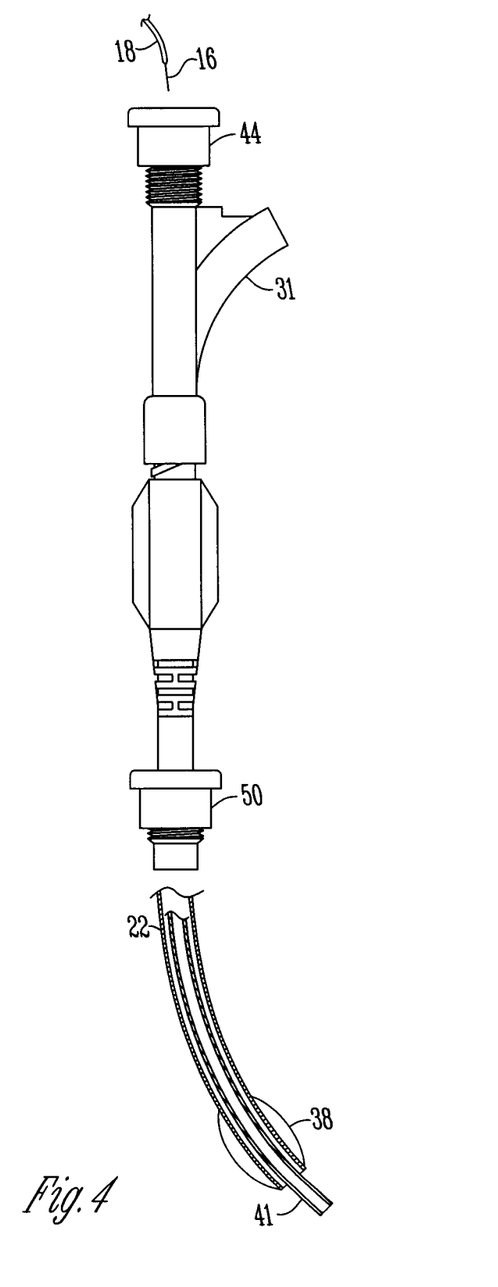
FIG. 4 is an enlarged scale sectional view of a catheter assembly.

FIG. 4 shows yet another alternative embodiment wherein the anchoring catheter 22 acts as a sleeve that fits over the guiding catheter 41. In this embodiment the guiding catheter 41 has a first valve element 44 through which the balloon dilation catheter 18 and guide wire 16 are passed. Additionally a second valve element 50 is fitted on the proximal end of the anchoring catheter 22 through which the guiding catheter 41 is passed while sliding the anchoring catheter 22 over the guiding catheter beginning at the distal tip of the guiding catheter 41 and working backwards. The second valve element 50 when tightened on the guiding catheter 41 secures the anchoring catheter 22 to the guiding catheter 41. Again, the use of multiple valve elements allows further control of the catheter assembly.

In this embodiment a funnel insert (not shown) may optionally be used to facilitate the placement of anchoring catheter 22 on the distal end of the guiding catheter 41 as a sleeve element. Specifically the funnel insert spreads open the anchoring catheter 22 to align the anchoring catheter 22 with the guiding catheter 41. Once aligned the funnel insert is withdrawn and the anchoring catheter 22 is placed over the guiding catheter 41. The funnel insert can similarly be used with the dual sheath design depicted in FIG. 5.

Figure 5:
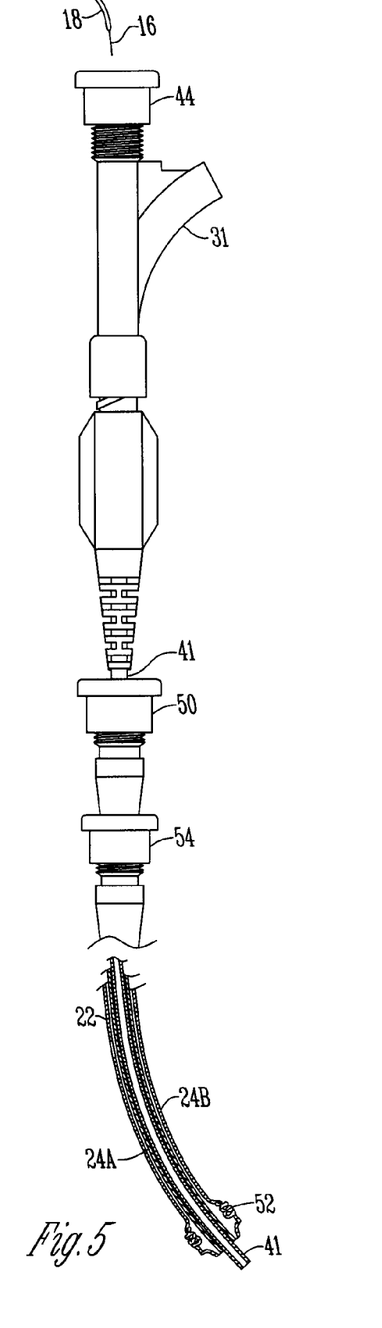
FIG. 5 is an enlarged scale sectional view of a catheter assembly.

In the embodiment shown in FIG. 5 the anchoring catheter is composed of inner and outer sheaths 24A and 24B that act like a sleeve placed over the guiding catheter 41 as is shown in FIG. 4. The guiding catheter 41 additionally has a first valve element 44 through which the balloon dilation catheter 18 and guide wire 16 would be placed into the guiding catheter 41. In this embodiment second and third valve elements 50, 54 are connected to the proximal ends of both the inner and outer sheaths 24A and 24B. In this way the second valve element 50 on the inner sheath 24A would fix its position relative to the guiding catheter 41 and would prevent blood from dripping back as well. The third valve element 54 on the outer sheath 24B would fix its position relative to the inner sheath and would prevent blood from dripping back through the outer sheath 24B.

Figure 6:
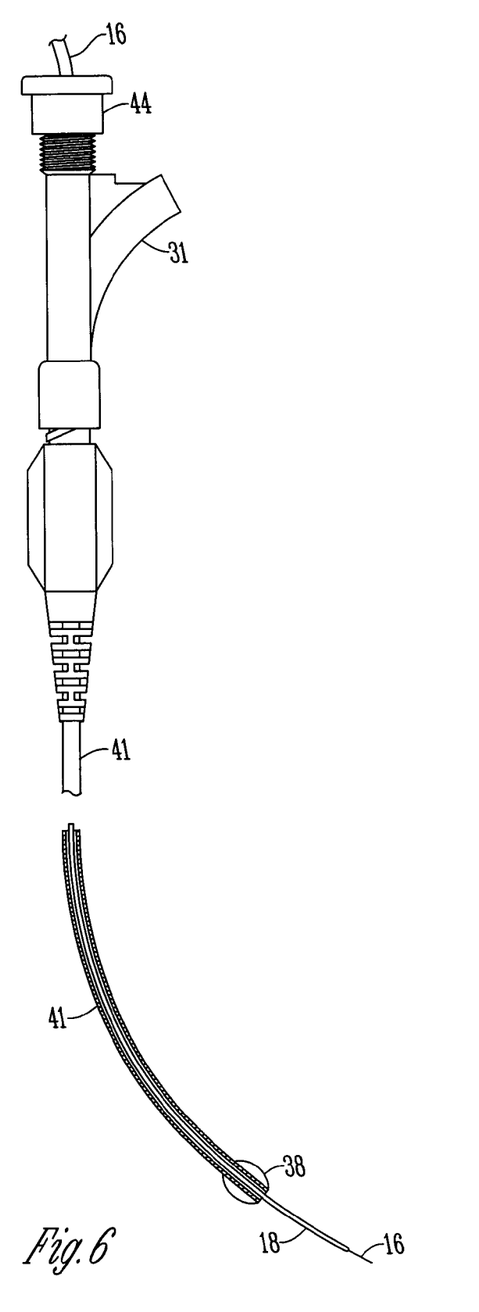
FIG. 6 is an enlarged scale sectional view of a catheter assembly.

FIG. 6 shows another alternative design wherein the anchoring catheter 22 and guiding catheter 41 are combined into a single catheter that is considered guide catheter 41. Thus, a valve element 44 is on the proximal end of the guiding catheter 41 to secure the balloon dilation catheter 18 and wire 16 therein. Additionally, the external balloon 38, when inflated within the coronary artery 14 anchors the guiding catheter 41 to the coronary artery 14. In this embodiment wherein sheaths are employed a section of expandable material 52 functions similar to the external balloon 38 of FIG. 6 as with other such embodiments.

Figure 7:
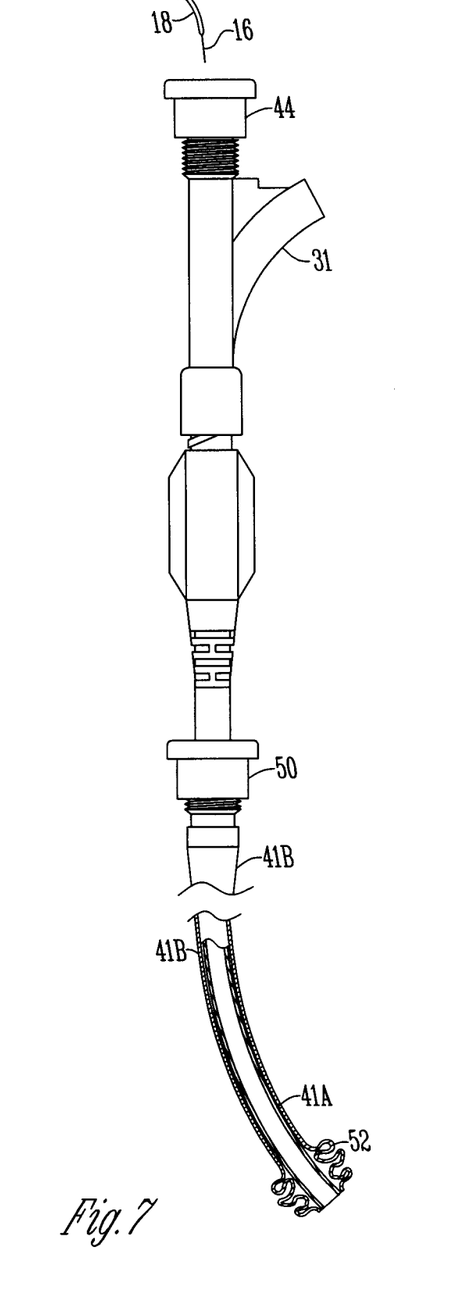
FIG. 7 is an enlarged scale sectional view of a catheter assembly.

In a final alternative embodiment as in the embodiment shown in FIG. 6, in FIG. 7 the anchoring and guiding catheters are combined to provide a single guiding catheter 41. In this embodiment the guiding catheter 41 has inner and outer sheaths 41A and 41B wherein a first valve element 44 is at the proximal end of the inner sheath 41A whereas a second valve element 50 is at the proximal end of the outer sheath 41B. Thus, the valve element 44 on the inner sheath 41A serves to prevent backflow of blood and additionally allows entry of the balloon dilatation catheter 18 and guide wire 16. Meanwhile, the second valve element 50 on the outer sheath 41B prevents backflow of blood and also secures the outer sheath 41B onto the inner sheath 41A locking the sheaths 41A and 41B into place.

The FIGS. 2-7 each show the use of side port 31 used in association with first and second valve elements 44, 50. Similarly, port 31 could be used in association with valve element 54. Additionally, while only a single side port is shown in each figure, a plurality of side ports could be used such that each valve element 44, 50 and 54 could have a side port 31 without falling outside the scope of this disclosure.

In operation, the guiding catheter 41 is inserted into the groin of the patient in the manner described above and positioned at the origin of the coronary artery 14. The balloon dilatation catheter 18 is inserted over guide wire 16, and both the guide wire 16 and balloon dilatation catheter 18 are then inserted within anchoring catheter 22. The assembled guide wire 16, balloon dilatation catheter 18 and anchoring catheter 22 are moved as a unit into guiding catheter 41. At this point in time, the external balloons 36 and 38 of anchoring catheter 22 are still deflated. The above described assembled components are extended through the guiding catheter until the guide wire 16 and the distal end of the anchoring catheter 22 extend distally beyond the distal end of the guiding catheter. At that point in time, the internal balloons 30 are deflated in the manner described by valve 42 and the external balloons 36 and 38 are inflated. The external balloon 38 engages the inner wall of coronary artery 14, while the external balloon 36 engages the interior of the guiding catheter 41. In other embodiments external balloons 36 or 38 are used. In either embodiment the guiding catheter 41 is secured to the coronary artery 14.

Additionally, when using valve elements 44, 50 or 54 the method includes securing either the catheters themselves together or the sheaths of the catheters together. Specifically, in one embodiment a valve element 44 can secure an anchoring catheter 22 to a guiding catheter 41 whereas in another embodiment the inner and outer sheaths of the anchor catheter 22 or inner and outer sheaths of a guiding catheter 41 are secured together. Similarly, the balloon dilatation catheter 18 and wire 16 can be secured to either an anchoring catheter 22 or a guiding catheter 41 using a valve element 44 depending on the needed application. By using the plurality of valve elements backflow of blood is prevented, and a plurality of arrangements allowing for better control of all catheters is presented.

Additional configurations of catheters are proposed. Various advantages are afforded by these different designs such as the anchoring catheter which slips over the guiding catheter allowing for universal adaptability to pre-existing guiding catheters, and catheters with distally positioned soft expandable material which may be softer and possibly more tenacious to the vessel wall than balloons, and the single catheter design which is advantageous in its simplicity with either a distal balloon or the use of distally positioned soft expandable material. Use of perfusion ports allows perfusion during the process of anchoring the guiding catheter to the coronary ostium. Lack of perfusion ports allows the anchoring catheter to be utilized for proximal embolic protection. Thus, at the very least all of the stated objectives have been met.

Although some descriptions of the invention referred to angioplasty systems, dilatation balloons, balloon dilatation catheters and treatment of coronary arteries, it should be understood that such elements are merely exemplary and the invention can be used in conjunction with a variety of treatment catheters and in different vessels of the human body. Treatment catheters can include treatment elements such as, for example, angioplasty balloons, stents, and stent delivery components and radiation therapy apparatuses. As well, it should be understood that the invention can be utilized in separate vein grafts and arterial bypass grafts. Additionally, the use of known catheter configurations is contemplated within the scope of this disclosure. For example, a side entry port as contemplated by U.S. Pat. Nos. 5,489,271 and 5,554,118 for insertion of catheters is contemplated without falling outside the scope of this disclosure.

It will be appreciated by those skilled in the art that other various modifications could be made to the device without the parting from the spirit and scope of this invention. All such modifications and changes fall within the scope of the claims and are intended to be covered thereby.

What is claimed is:

1. A catheter assembly comprising:
   a hollow guiding catheter having a distal end and a proximal end;

a hollow anchoring catheter extensible through the guiding catheter and having a distal end and a proximal end with a wall having an inner sheath and an outer sheath with an expandable material disposed therebetween the inner sheath and the outer sheath;

a dilatation catheter extensible through the inner sheath of the anchoring catheter;

a guide wire extending through the dilatation catheter and along which the dilatation catheter is slidable;

a valve element attached to the guiding catheter having a valve opening therein through which the anchoring catheter is extensible;

wherein when actuated the valve element secures the anchoring catheter therein and prevents back flow of blood; and wherein the inner sheath and outer sheath slide over each other to radially retract and expand the expandable material disposed between the inner and outer sheaths such that the inner sheath extends past the outer sheath to expose a section of the expandable material which radially expands to engage the guide catheter or a blood vessel.

2. The catheter assembly of claim 1 wherein the valve element is a Tuohy-Borst valve.

3. The catheter assembly of claim 1 wherein the anchoring catheter has a side wall having a fluid port attached thereto.

4. The catheter assembly of claim 1 further comprising a valve element attached to the inner sheath.

5. The catheter assembly of claim 1 wherein the outer sheath slides in relation to the inner sheath to retract and expand a section of the expandable material.

6. The catheter assembly of claim 1 wherein the expandable material is positioned between the distal end of the anchoring catheter and the distal end of the guiding catheter.

7. The catheter assembly of claim 2 wherein the inner sheath and outer sheath are positioned adjacent the distal end of the anchoring catheter.

8. The catheter assembly of claim 1 wherein the expandable material is positioned adjacent the distal end of the anchoring catheter.

9. The catheter assembly of claim 1 wherein the expandable material is a material that is softer and more tenacious to a blood vessel wall than balloons.

10. The catheter assembly of claim 1 wherein the expandable material is a porous material to permit blood flow through the blood vessel and prevent occlusion of blood flow through the vessel upon expansion of the expandable material.

11. The catheter assembly of claim 1 wherein the anchoring catheter includes perfusion ports located proximal or proximal and distal to the section of expandable material.

12. A catheter assembly comprising:

a hollow guiding catheter having a distal end and a proximal end;

a hollow anchoring catheter extensible through the guiding catheter and having a distal end and a proximal end with a wall having an inner sheath and an outer sheath with an expandable material disposed therebetween the inner sheath and the outer sheath;

a dilatation catheter extensible through the inner sheath of the anchoring catheter;

a guide wire extending through the dilatation catheter and along which the dilatation catheter is slidable;

a valve element attached to the guiding catheter having a valve opening therein through which the anchoring catheter is extensible;

wherein when actuated the valve element secures the anchoring catheter therein and prevents back flow of blood;

wherein the inner sheath and outer sheath slide over each other to radially retract and expand the expandable material disposed between the inner and outer sheaths such that the inner sheath extends past the outer sheath to expose a section of the expandable material which radially expands to engage the guide catheter or a blood vessel; and wherein the anchoring catheter includes perfusion ports located proximal or proximal and distal to the section of expandable material.

13. A catheter assembly comprising:

a hollow guiding catheter having a distal end and a proximal end;

a hollow anchoring catheter extensible through the guiding catheter and having a distal end and a proximal end with a wall having an inner sheath and an outer sheath with an expandable material disposed therebetween the inner sheath and the outer sheath;

a dilatation catheter extensible through the inner sheath of the anchoring catheter;

a guide wire extending through the dilatation catheter and along which the dilatation catheter is slidable;

a valve element attached to the guiding catheter having a valve opening therein through which the anchoring catheter is extensible;

wherein when actuated the valve element secures the anchoring catheter therein and prevents back flow of blood;

wherein the inner sheath and outer sheath slide over each other to radially retract and expand the expandable material disposed between the inner and outer sheaths such that the inner sheath extends past the outer sheath to expose a section of the expandable material which radially expands to engage the guide catheter or a blood vessel; and wherein the expandable material is a porous material to permit blood flow through the blood vessel and prevent occlusion of blood flow through the vessel upon expansion of the expandable material.

* * * * *